(12) United States Patent  (10) Patent No.: US 7,623,974 B2
Cipra  (45) Date of Patent: Nov. 24, 2009

(54) SYSTEM AND METHOD FOR DETECTING ONSET OF STRUCTURAL FAILURE

(75) Inventor: Dale O. Cipra, Chatsworth, CA (US)

(73) Assignee: Pratt & Whitney Rocketdyne, Inc., Canoga Park, CA (US)

( * ) Notice: Subject to any disclaimer, the term of this patent is extended or adjusted under 35 U.S.C. 154(b) by 80 days.

(21) Appl. No.: 11/699,945

(22) Filed: Jan. 30, 2007

(65) Prior Publication Data

US 2008/0183403 A1    Jul. 31, 2008

(51) Int. Cl.
G06F 3/00 (2006.01)
(52) U.S. Cl. .............................. 702/41; 702/33; 702/42; 702/76
(58) Field of Classification Search ................. 702/33, 702/39, 77, 81, 127, 150, 185, 41, 42, 76; 324/524; 385/12, 13; 701/29; 73/582, 583
See application file for complete search history.

(56) References Cited

U.S. PATENT DOCUMENTS

| | | | |
|---|---|---|---|
| 4,901,575 A * | 2/1990 | Bohannan et al. ............. 73/587 |
| 5,195,046 A | 3/1993 | Gerardi et al. |
| 5,347,190 A * | 9/1994 | Lewis et al. ................. 310/90.5 |
| 5,913,246 A | 6/1999 | Simonelli et al. |
| 6,006,163 A * | 12/1999 | Lichtenwalner et al. ....... 702/36 |
| 6,539,809 B1 | 4/2003 | Weiss et al. |
| 6,631,647 B2 | 10/2003 | Seale |
| 7,013,223 B1 | 3/2006 | Zhang et al. |
| 7,024,315 B2 | 4/2006 | Giurgiutiu |
| 7,103,507 B2 * | 9/2006 | Gorinevsky et al. ......... 702/184 |
| 7,174,255 B2 * | 2/2007 | Giurgiutiu et al. ............ 702/35 |
| 7,283,693 B2 * | 10/2007 | Menendez Martin et al. .. 385/13 |

OTHER PUBLICATIONS

Jeongyeup Paek, Krishna Chintalapudi, Ramesh Govindan, John Caffey, Sami Masri; A Wireless Sensor Network for Structural Health Monitoring: Performance and Experience; May 2005.

* cited by examiner

Primary Examiner—Eliseo Ramos Feliciano
Assistant Examiner—Felix E Suarez
(74) Attorney, Agent, or Firm—Kinney & Lange P.A.

(57) ABSTRACT

A system for detecting the onset of structural failure in a structural element subject to a mechanical load comprises a metering array, a signal processor, and an output processor. The metering array measures physical quantities associated with the structural element. The signal processor transforms the measured physical quantities into a series of sample mode spectra, and the output processor generates output as a function of the series of sample mode spectra. Methods are also disclosed for detecting the onset of failure in a structural element subject to a mechanical load, for structural testing, and for structural health monitoring.

38 Claims, 13 Drawing Sheets

SYSTEM AND METHOD FOR DETECTING ONSET OF STRUCTURAL FAILURE

BACKGROUND OF THE INVENTION

The present invention relates generally to structural testing and structural monitoring, and in particular to detecting the onset of structural failure by analysis of sample oscillation mode spectra.

Structural failure can be unpredictable and catastrophic, posing both financial risk and a threat to personal and public safety. Traditional destructive testing techniques are effective at determining a failure threshold, but cannot generally detect the onset of failure before it occurs. As a result, safety margins must be determined a priori or by trial and error.

This presents a significant problem for non-destructive testing, in which unanticipated structural failure can result in both economic loss and safety hazards. Post-testing failures (i.e., during construction or use) may be even more serious, but are even more difficult to predict.

Traditional structural inspection techniques suffer from limited accessibility and require significant time and expertise. This forces an economic tradeoff between the inspection cycle and its cost, resulting in inspections that are at best periodic, or that occur only after a significant event such as earthquake, fire, or accident. Moreover, traditional inspection techniques tend to rely on visual surveys which are quite different from the methods employed during structural testing. This makes correlation between the two approaches difficult, further compromising the ability of traditional structural testing and inspection to detect the onset of structural failure before it actually occurs.

Structural health monitoring (SHM) systems address some of these concerns. SHM systems employ a variety of sensing and measurement technology, utilizing generally small, remotely-operated sensors. These provide information on position, temperature, and other physical quantities, and allow for continuous monitoring in otherwise inaccessible locations. SHM systems may also employ active ultrasonic transducers to "interrogate" a structure or material, to detect displacement, delamination, cracking, or other local failures via the resulting change in Lamb wave transmissions.

Nonetheless prior art SHM utility remains limited because the systems do not apply the same monitoring techniques as those used during structural testing, and because the prior art cannot detect the onset of failure before it has occurred, at least on a local scale. There thus remains a need for a more integrated and forward-looking approach to structural testing and structural health monitoring.

BRIEF SUMMARY OF THE INVENTION

This invention concerns a system and method for detecting the onset of failure in a structural element subject to a mechanical load. The system includes a metering array that measures physical quantities associated with the structural element, a signal processor that transforms the measured physical quantities into a series of sample mode spectra, and an output processor that generates output based on a function of the series of sample mode spectra.

In one embodiment, the load is substantially compressive, the measurements characterize acceleration, and the transformation comprises a fast Fourier transform. In this embodiment the sample mode spectra characterize a fundamental mode of oscillation, and the output comprises an alarm based upon an alarm-generating function of the series of sample mode spectra.

Alternatively, the mechanical load may be a more general stress, strain, tension, torsion, pressure, or other mechanical load, or a combination of loads, and the corresponding measurements may relate to position, velocity, acceleration, angle, stress, strain, tension, torsion, vibrational frequency, temperature, pressure, or other physical quantity. Further, sampling characteristics such as scale sensitivity, period, integration time, and transformation window may be determined a priori, or adjusted according to a series of baseline spectra.

DETAILED DESCRIPTION

Figure 1:
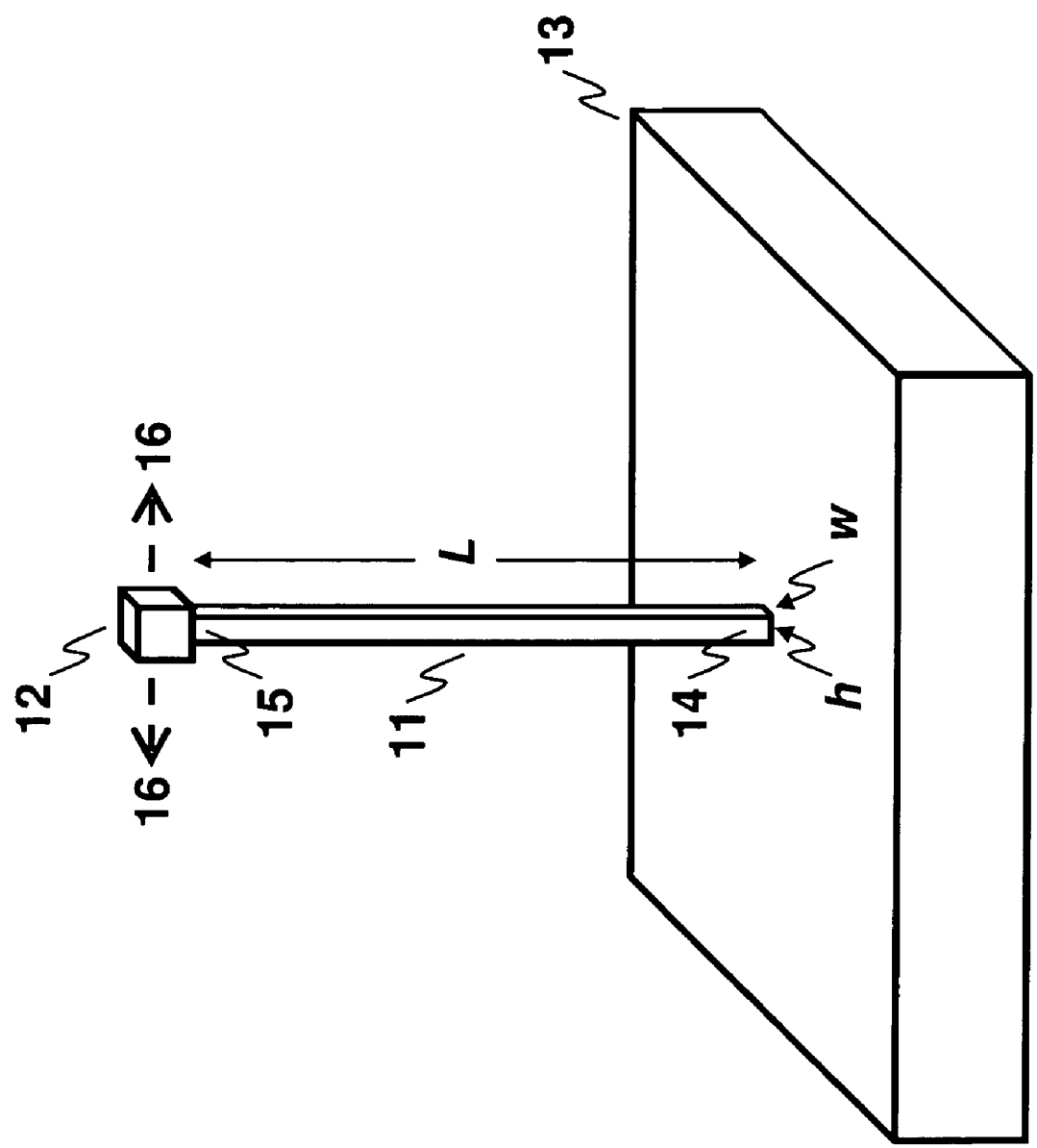
FIG. 1 is a perspective view of a vertical cantilevered beam subject to a compressive load.

FIG. 1 is a perspective view of vertical cantilevered beam 11 subject to compressive load 12. FIG. 1 shows cantilevered beam 11 of length L with transverse dimensions h and w, loading mass 12 with mass m, and immobile base 13. Beam 11 is vertically oriented, with lower end of beam 14 affixed to base 13 and upper end of beam 15 affixed to loading mass 12. Beam 11 has small mass as compared to mass m of loading mass 12, and loading mass 12 has small dimensions as compared to length L of beam 11.

In this arrangement, loading mass 12 and upper end 15 of beam 11 are susceptible to small-amplitude oscillations generally contained in a horizontal plane parallel to base 13.

Arrows 16 indicate one possible sense of this oscillation, which is spring-like with natural frequency f determined by effective spring constant k and mass m:

$$f = \frac{1}{2\pi}\sqrt{\frac{k}{m}}. \quad (1)$$

The effective spring constant k characterizes the stiffness of the beam. For a vertically cantilevered beam the spring constant is $$k = 3\frac{EI}{L^3}, \quad (2)$$

where E is Young's modulus, I is the second moment of area, and L is the length of the beam.

Young's modulus is also known as the elastic modulus. It characterizes the intrinsic stiffness of the material from which the beam is made, and has units of pressure. Young's modulus ranges from about 11 GPa ($11 \cdot 10^9$ pascal) for oak to just under 70 GPa for aluminum, and from approximately 190-210 GPa for iron and steel alloys.

Beam geometry contributes independently to the stiffness via the second moment of area I, also known as the area moment of inertia. For a rectangular beam the second moment of area I is determined by the beam's cross-sectional dimensions:

$$I = \frac{wh^3}{12}. \quad (3)$$

In general, w is measured perpendicularly to the direction of oscillation and h is measured parallel to it. For a horizontal cantilever, with oscillations in a generally vertical plane, h is simply the height of the beam while w is the width. For the vertical cantilever of FIG. 1 both h and w are measured horizontally, but the definitions are the same.

Combining Eqs. 1-3, the natural frequency of oscillation f for a vertical cantilevered beam of length L with Young's modulus E and rectangular dimensions w and h, supporting mass m, is:

$$f = \frac{1}{4\pi}\sqrt{\frac{Ewh^3}{mL^3}}. \quad (4)$$

This equation characterizes the natural frequency of small-amplitude, generally horizontal oscillations of loading mass 12 and upper end 15 of vertical cantilevered beam 11, where beam 11 has small mass as compared to loading mass 12, and loading mass 12 has small dimensions as compared to beam length L. Eq. 4 characterizes the fundamental mode of oscillation for this system, which mode exhibits the lowest natural frequency.

Eq. 4 is illustrative of other modes, both fundamental and higher-order, as exhibited by a wide range of structural elements. It is possible to detect the onset of failure in such structural elements because the oscillations characterized by Eq. 4 will diverge from their natural frequencies in the region prior to actual failure, due to a load-dependent shift in the natural frequency response.

Figure 2:
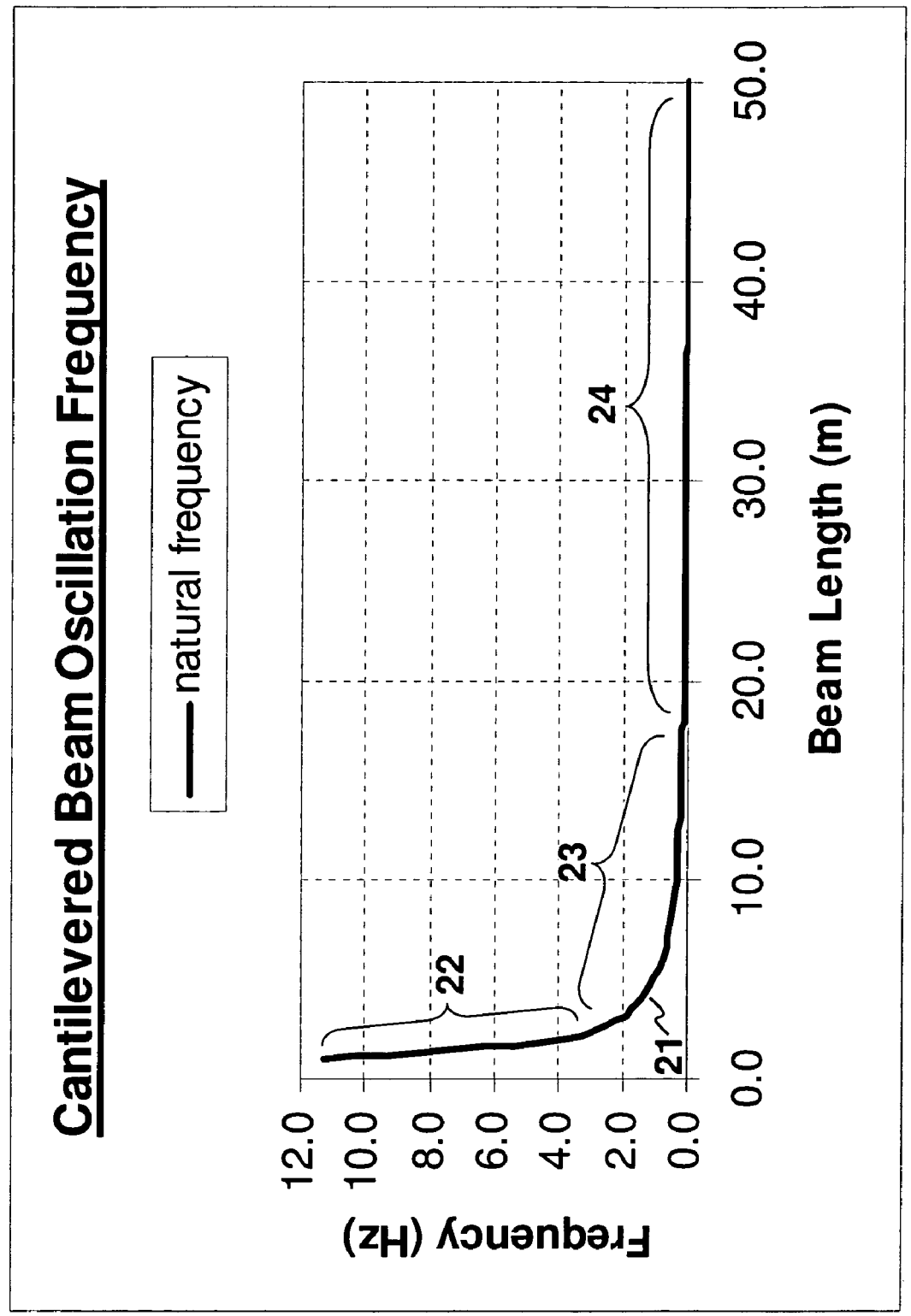
FIG. 2 is a plot of natural oscillation frequency as a function of cantilever length, neglecting the effect of load on frequency.

FIG. 2 is a plot of natural oscillation frequency as a function of cantilever length, neglecting the effect of load on frequency. The figure shows natural frequency curve 21 for a steel alloy beam with Young's modulus E=200 GPa. The beam has rectangular cross section with w=h=0.10 m, and supports mass m=1,000 kg.

Natural frequency curve 21 varies smoothly with length over the entire displayed domain. The curve declines rapidly through region 22, from f>10 Hz for L=1 m to f<1.0 Hz for L=10.0 m, then more slowly through intermediate region 23 until it approaches f=0.0 Hz in asymptotic region 24, where L may increase arbitrarily.

Real beams do not exhibit this asymptotic behavior. Instead, as L approaches a critical point, the observed frequency will depart from natural frequency curve 21 until the system reaches a critical point, where the observed frequency drops to zero and the beam suffers a buckling failure.

Buckling failures are particularly problematic because they are both hazardous and difficult to predict. The capability to detect the onset of a buckling failure is therefore an important advantage, but buckling failures are only a particular representation of the range of failure modes to which the techniques described herein may be applied.

Figure 3:
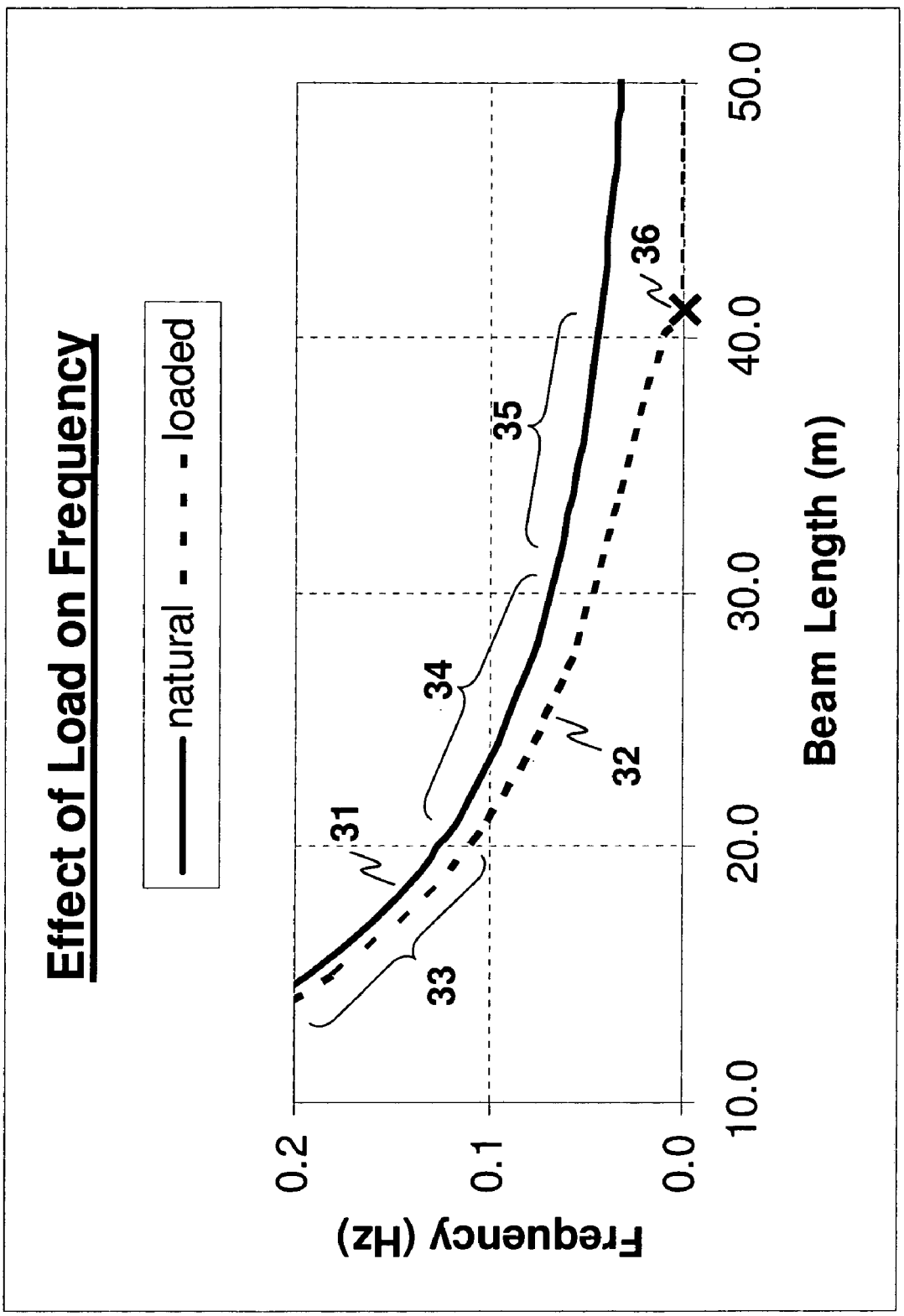
FIG. 3 is an enlarged view of FIG. 2, showing the effect of load on frequency near critical length.

FIG. 3 is an enlarged view of FIG. 2, showing the effect of load on frequency near critical length. The figure shows both natural frequency curve 31 and more realistic mechanically loaded curve 32. Curves 31 and 32 agree relatively well through region 33, where L<20 m, but the curves separate in intermediate region 34 and strongly diverge in region 35, where L>30 m. At critical point 36 the loaded curve 32 drops to zero, indicating failure, whereas the idealized or natural frequency curve 31 continues on.

Note that both natural frequency curve 31 and loaded curve 32 account for the mass m via the natural frequency equation (Eq. 1). Their divergence arises because loaded curve 32 also accounts for the compressive (gravitational) load on the beam which has an independent effect on the frequency. This loading effect is small in region 33, far from criticality, but increases through transition region 34 and begins to dominate in strongly diverging region 35, until loaded curve 32 goes abruptly to zero at critical point 36.

The difference between natural frequency f and more realistic or loaded frequency $f_l$ is characterized by the ratio of loading force F to critical load $F_c$, as described by Timoshenko, Young and Weaver:

$$f_l = f\sqrt{1 - \frac{F}{F_c}}. \quad (5)$$

The loading force is the gravitational force F=mg on loading mass m, and the critical load is given by Euler's formula in terms of Young's modulus E, second moment of area I, and length L:

$$F_c = \frac{EI\pi^2}{L^2}. \quad (6)$$

If the load is fixed, Euler's formula can be interpreted in terms of a critical length $L_c$. This is the length at which (fixed) gravitational load F=mg becomes sufficient to cause structural failure; that is, $$L_c = \pi \sqrt{\frac{EI}{mg}}.\quad(7)$$

When $L=L_c$, loading force F equals critical force $F_c$ and the Timoshenko, Young and Weaver equation (Eq. 5) yields zero frequency. There are moreover no real solutions for $L>L_c$, indicating structural failure.

More general loading forces yield the same result; that is, regardless of failure mode, the loaded frequency $f_l$ goes rapidly to zero when the load becomes critical, and there are no real solutions for $F>F_c$. Thus the technique applies not only to compressive loads but also to more general stress, strain, tension, torsion, pressure, or other mechanical loads.

Figure 4:
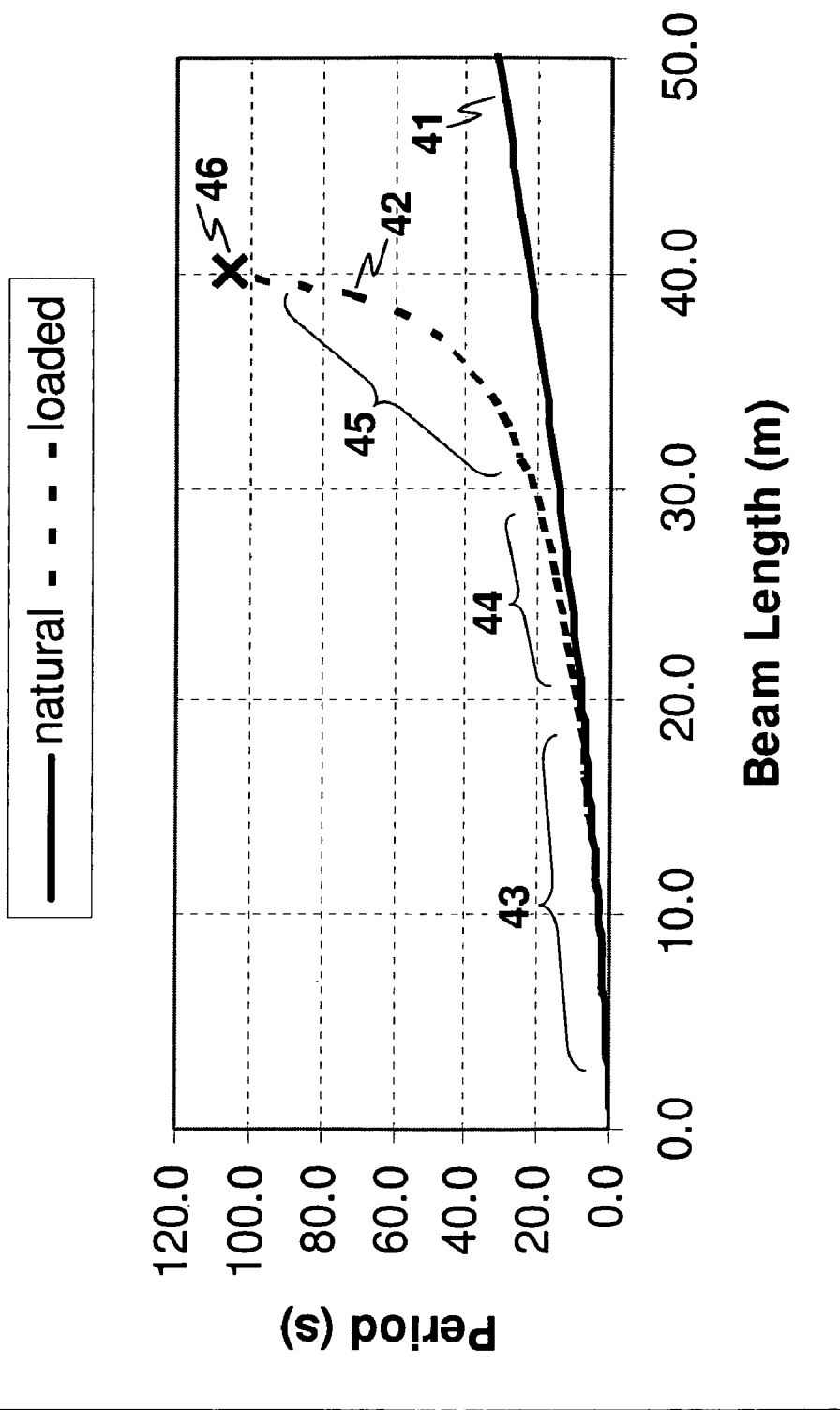
FIG. 4 is a plot of oscillation period as a function of cantilever length, showing the effect of load on natural period of oscillation.

FIG. 4 is a plot of oscillation period as a function of cantilever length, showing the effect of load on natural period of oscillation. FIG. 4 shows natural oscillation curve 41 and loaded curve 42, which are the inverses of frequency curves 31 and 32, respectively (that is, the natural period is T=1/f and the loaded period is $T_l=1/f_l$). The beam is a steel alloy beam with the same characteristics described above with respect to FIG. 2.

As in the frequency plot of FIG. 3, above, curves 41 and 42 exhibit similar region 43, intermediate region 44, and strongly diverging region 45 just prior to critical point 46. In contrast to FIG. 3, however, period curve 42 becomes unbounded at critical point 46, rather than approaching zero. While the underlying mathematics are the same as for the frequency analysis, the inverse or period analysis nonetheless illustrates the fundamentally different behavior of natural oscillation curve 41 and loaded oscillation curve 42 in the approach to criticality.

FIG. 4 also shows a clear separation between natural oscillation curve 41 and loaded curve 42 in intermediate region 44, a key advantage of the technique. While the onset of structural failure may be most obvious near critical point 46, it is also indicated in intermediate region 44, well before criticality and even before reaching strongly diverging region 45. Thus the onset of structural failure can be detected not only before failure actually occurs, but also before its local manifestations such as delamination or cracking.

Figure 5:
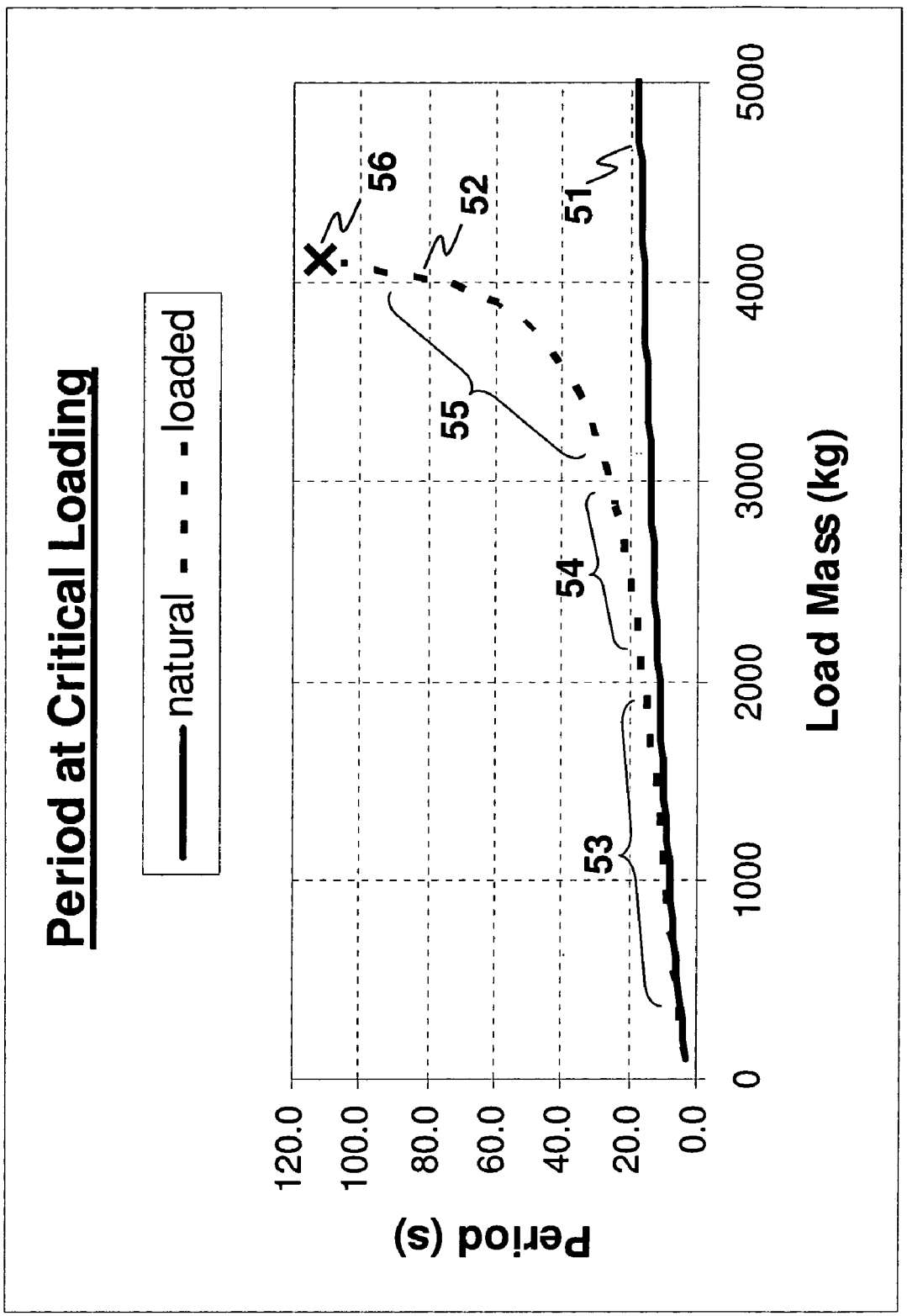
FIG. 5 is a plot of oscillation period as a function of compressive load, showing the effect of load on natural period of oscillation.

FIG. 5 is a plot of oscillation period as a function of compressive load, showing the effect of load on natural period of oscillation. FIG. 5 shows natural oscillation curve 51 and loaded curve 52, for a beam with fixed length L=10 m, variable loading mass m, and other characteristics as described with respect to FIG. 2.

Natural oscillation curve 51 and loaded curve 52 again pass through similar region 51, transition region 52, and strongly diverging region 53 before reaching critical point 56. In FIG. 5, however, the divergence depends directly upon loading mass m, not indirectly upon length L. This illustrates the capability to detect the onset of structural failure whether due to a change in actual load, or due to a change in some other physical parameter such as cantilever length, pressure, or temperature, which parameter affects the structural element's ability to sustain the load.

This technique may be beneficially applied to three general classes of structural elements. In the first class, the natural oscillation curve can be analytically modeled, but the failure points are unknown. In this class, the loaded curves cannot be predicted but they may be measured, and can signal the onset of structural failure by departure from the natural oscillation model. Analysis of the loaded (measured) curve's departure can moreover provide a quantitative estimate of the critical point, obtainable from (modeled) natural frequency f and (measured) loaded frequency f by inverting the Timoshenko, Young and Weaver equation (Eq. 5).

In the second class, both the natural frequency and failure points may be known, providing an analytical model for both natural and loaded curves. In this class a measured oscillation curve may still help characterize the onset of an expected failure mode by departure from the (predicted) loaded curve. A sufficiently large departure may moreover signal an unexpected failure mode, due to manufacturing or construction defects, improper maintenance, environmental extremes, unanticipated loading conditions, or other unforeseen effect.

The third class covers structural elements for which no sufficiently predictive analytical model exists. This class may include composite structural elements made up Of a number of individual structural elements, structural elements of unknown construction or composition, or complex structural elements resistant to an analytical approach. As evident in FIGS. 3-5, however, and from the Timoshenko, Young and Weaver equation (Eq. 5), the slope of the loaded curve will nonetheless become unbounded as the structural element approaches criticality. Such behavior indicates the onset of structural failure even where no analytical model is available. Alternatively, slope analysis provides an additional failure indicator for structural elements in the first and second classes.

Figure 6A:
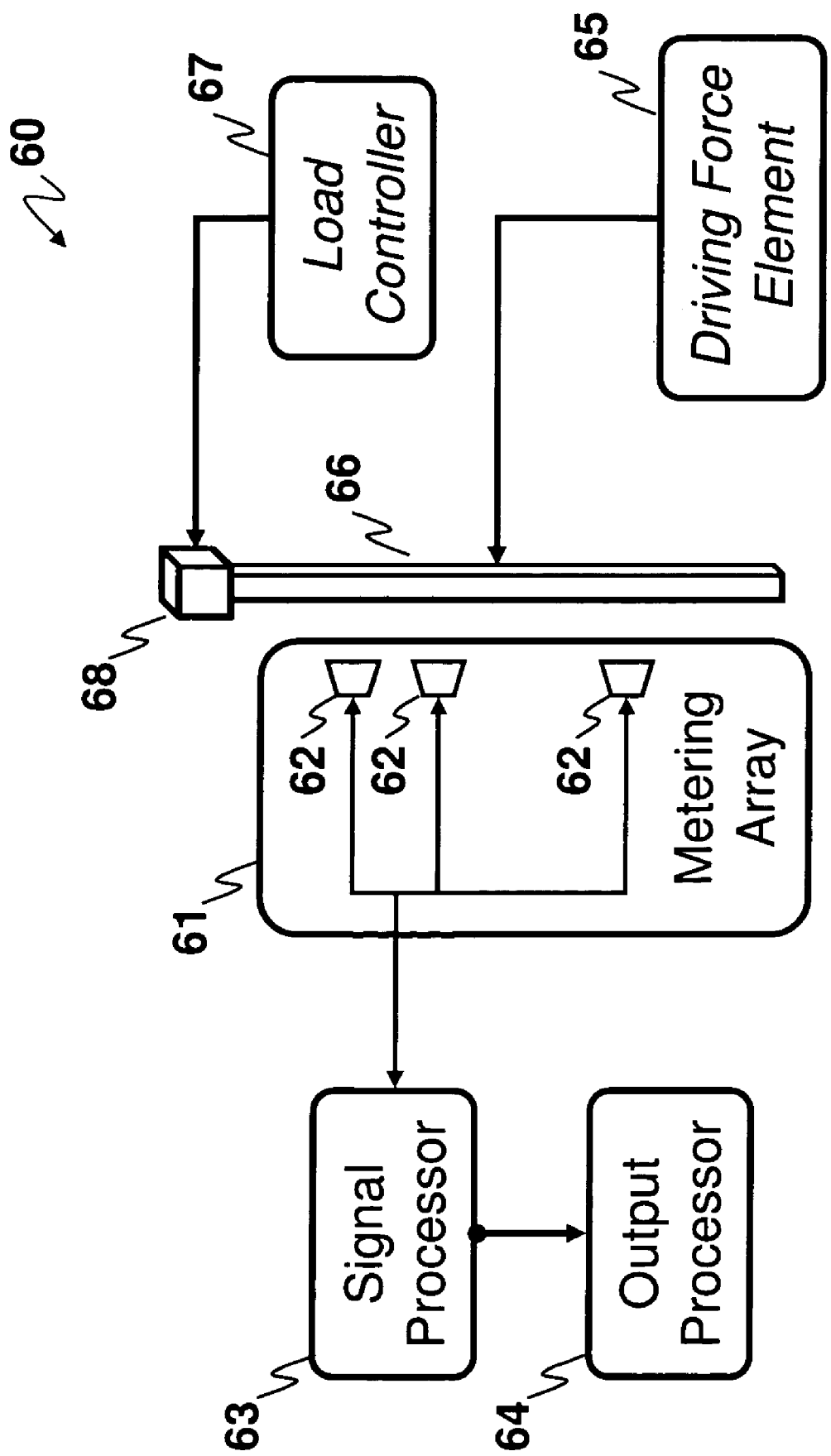
FIG. 6A is a block diagram of a system according to this invention, for detecting the onset of failure in a structural element subject to a mechanical load.
Figure 6B:
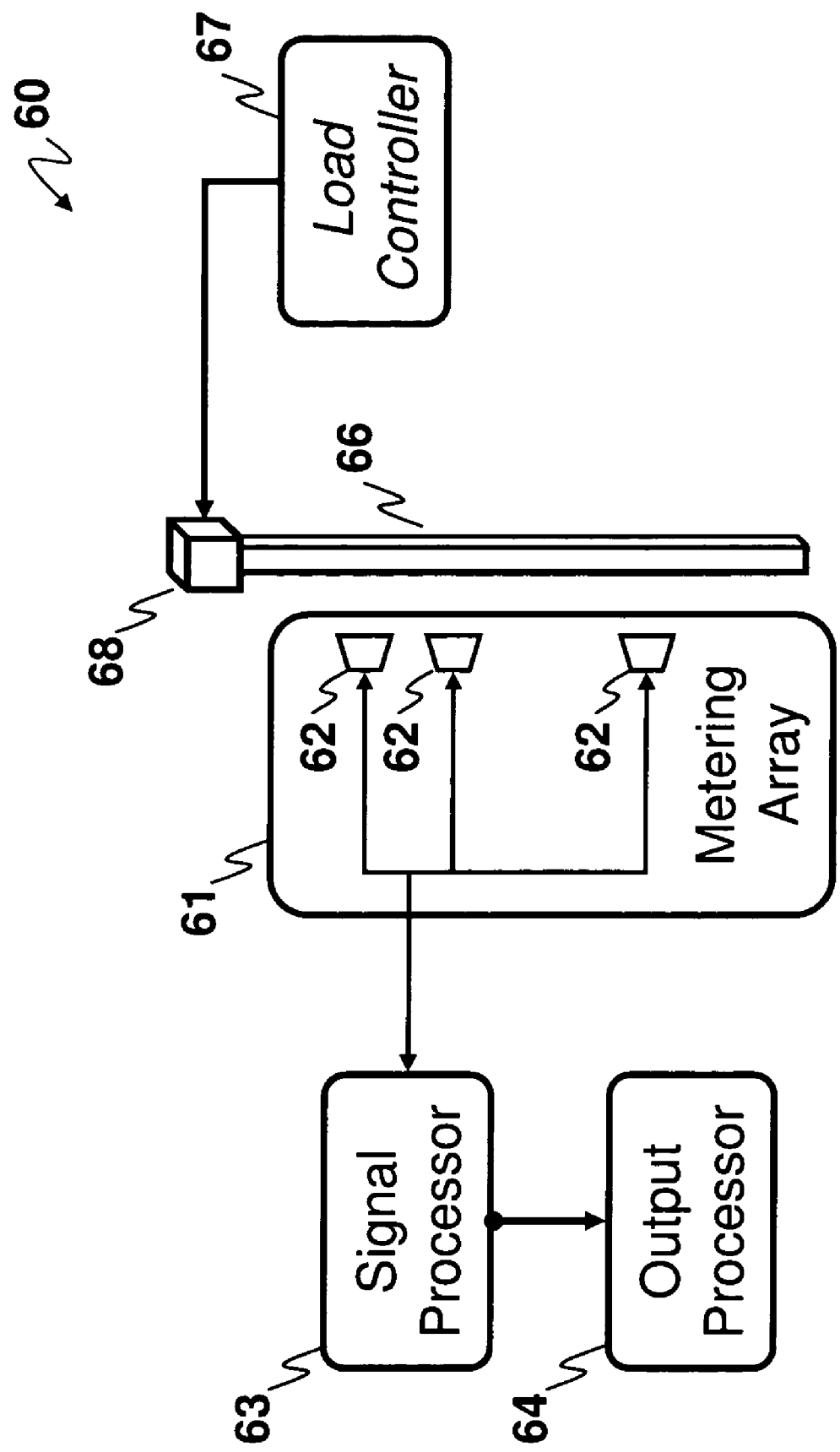
FIG. 6B is a block diagram of a system according to this invention, for detecting the onset of failure in a structural element subject to a mechanical load, where the system does not comprise a driving force element.
Figure 6C:
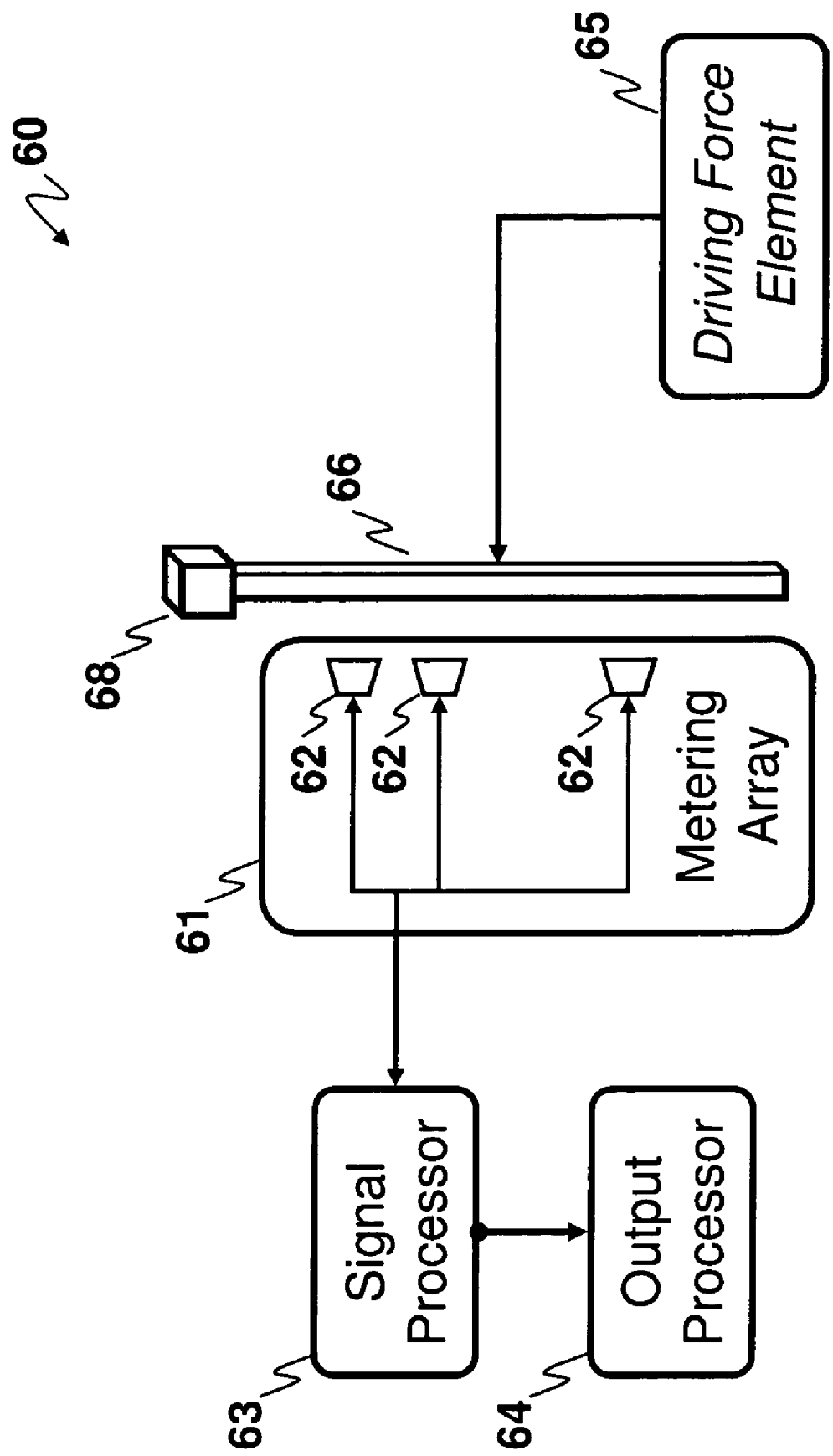
FIG. 6C is a block diagram of a system according to this invention, for detecting the onset of failure in a structural element subject to a mechanical load, where the system does not comprise a load controller.
Figure 6D:
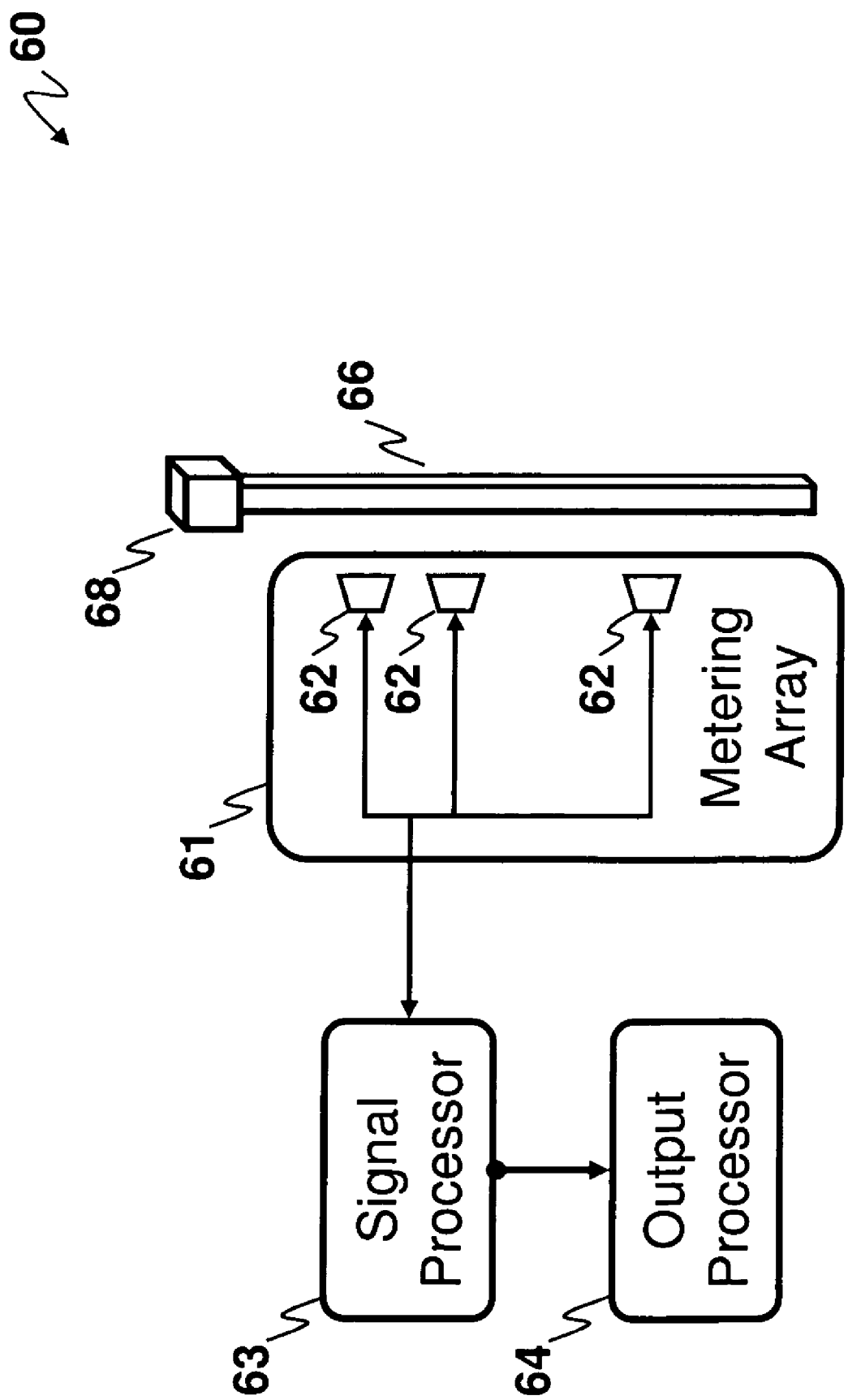
FIG. 6D is a block diagram of a system according to this invention, for detecting the onset of failure in a structural element subject to a mechanical load, where the system does not comprise a driving force element and the system does not comprise a load controller.

FIG. 6A is a block diagram of a system 60 for detecting the onset of failure in a structural element subject to a mechanical load. System 60 comprises metering array 61 with sensor elements 62, signal processor 63, output processor 64, driving force element 65, structural element 66, load controller 67 and mechanical load 68. In a first alternate embodiment shown in FIG. 6B, system 60 does not comprise driving force element 65. In a second alternate embodiment shown in FIG. 6C, system 60 does not comprise load controller 67. In a third alternate embodiment shown in FIG. 6D, system 60 does not comprise driving force element 65 and system 60 does not comprise load controller 67.

Metering array 61 comprises one or more sensor elements 62, which may be position sensors, velocity sensors, accelerometers, angular sensors, stress gauges, strain gauges, subsonic sensors, audio sensors, ultrasonic sensors, laser vibrometers, optical sensors, temperature sensors, pressure sensors or other sensing elements.

Signal processor 63 comprises a signal transform for transforming some metering array 61 measurements into a series of sample mode spectra. The signal transform may be, for example, a fast Fourier transform. Signal processor 63 also comprises an averaging transform for transforming other metering array 61 measurements into physical parameters. Optionally, signal processor 63 further comprises a metering array controller for controlling the metering array. The metering array controller may be custom designed, or a commercial product available for controlling metering array 61 and sensor elements 62.

Output processor 64 comprises a function of the series of sample mode spectra. The function characterizes oscillation modes of the structural element with respect to time, load, or other physical parameters upon which the modes depend. Optionally, the function includes an alarm-generating function of the series of sample mode spectra. The alarm generated may be an audible, visual, or electronic alarm, or a combination of alarms. In a preferred embodiment, output processor 64 comprises the same electronic components as signal processor 63, but the processors may also comprise distinct electronic components.

In an embodiment that comprises driving force element 65, driving force element 65 comprises a hammer, mechanical oscillator, or other forcing element capable of mechanical coupling to structural element 66. In an embodiment that comprises load controller 67, load controller 67 may be custom designed or may be a commercial product available for controlling mechanical load 68.

Structural element 66 is representative of a range of structural elements including a beam, post, pipe, wall, pressure vessel, vane, blade, housing, or other structural element, or a composite structural element composed of other structural elements. Structural element 66 is subject to mechanical load 68. Mechanical load 68 may be a compressive load, a more general stress, strain, tension, torsion, pressure, or other mechanical load, or a combination of mechanical loads. Mechanical load 68 may be constant or variable. Mechanical load 68 may be environmentally induced, or, in an embodiment that comprises load controller 67, mechanical load 68 may be controlled by load controller 67.

In operation of system 60, metering array 61 with sensor elements 62 is positioned for measuring physical quantities, and in particular oscillations, associated with structural element 66. The oscillations may be environmentally induced, or, in all embodiment that comprises driving forces element 65, the oscillations may be induced by driving force element 65. Advantageously, the oscillations are characteristic of the structural element and are not limited to any particular frequency range. They may be subsonic (e.g., fundamental mode oscillations of large structural elements), audio frequency (higher-order oscillation modes or oscillations of smaller structural elements), or ultrasonic (for small structural elements with high effective spring constants).

Metering array 61 communicates with signal processor 63 via transmission wires, cables, wireless systems, infrared systems, optical systems, or other communication means known to those skilled in the art. Optionally, the communications means is bi-directional. In this embodiment signal processor 63 may control a set of sampling characteristics such as scale sensitivity, period, integration time, and transformation window in order to provide increased sensitivity to the onset of failure in a particular structural element.

Signal processor 63 transforms some metering array 61 measurements into a series of sample mode spectra via a signal transform. In a preferred embodiment the signal transform is a fast Fourier transform, but the transform may also comprise a more general transform such as a wavelet transform. The series of sample mode spectra characterize physical oscillations in position, velocity, acceleration, angle, stress, strain, tension, torsion, temperature, pressure, or other physical quantity. Optionally, signal processor 63 may transform some metering array 61 measurements into a series of baseline mode spectra, and some metering array 61 measurements into a series of sample mode spectra.

Signal processor 63 also transforms other metering array 61 measurements into physical parameters via an averaging transform. Physical parameters do not characterize oscillations but instead characterize load, cantilever length, temperature, time, or other physical quantity upon which oscillations may depend. The determination of which measurements are appropriate for signal transform into spectra, and which are appropriate for averaging transform into physical parameters, will depend upon the characteristic oscillation modes of the relevant structural element.

Output processor 64 generates output as a function of the sample mode spectra and physical parameters. Output processor 64 acts analogously to the discussion of FIGS. 2-5, above, such that the output characterizes oscillation frequency curves or oscillation period curves. The output may characterize a fundamental mode or a higher-order mode, and may characterize the mode in terms of load, cantilever length, temperature, time, or other physical parameter upon which the mode may depend. Optionally, the output may include an alarm based upon an alarm-generating function of the series of sample mode spectra. The alarm-generating function may comprise a variation with respect to an analytical model, a variation with respect to a series of baseline spectra, a derivative of the series of sample mode spectra, or a composite function of such functions.

Figure 7A:
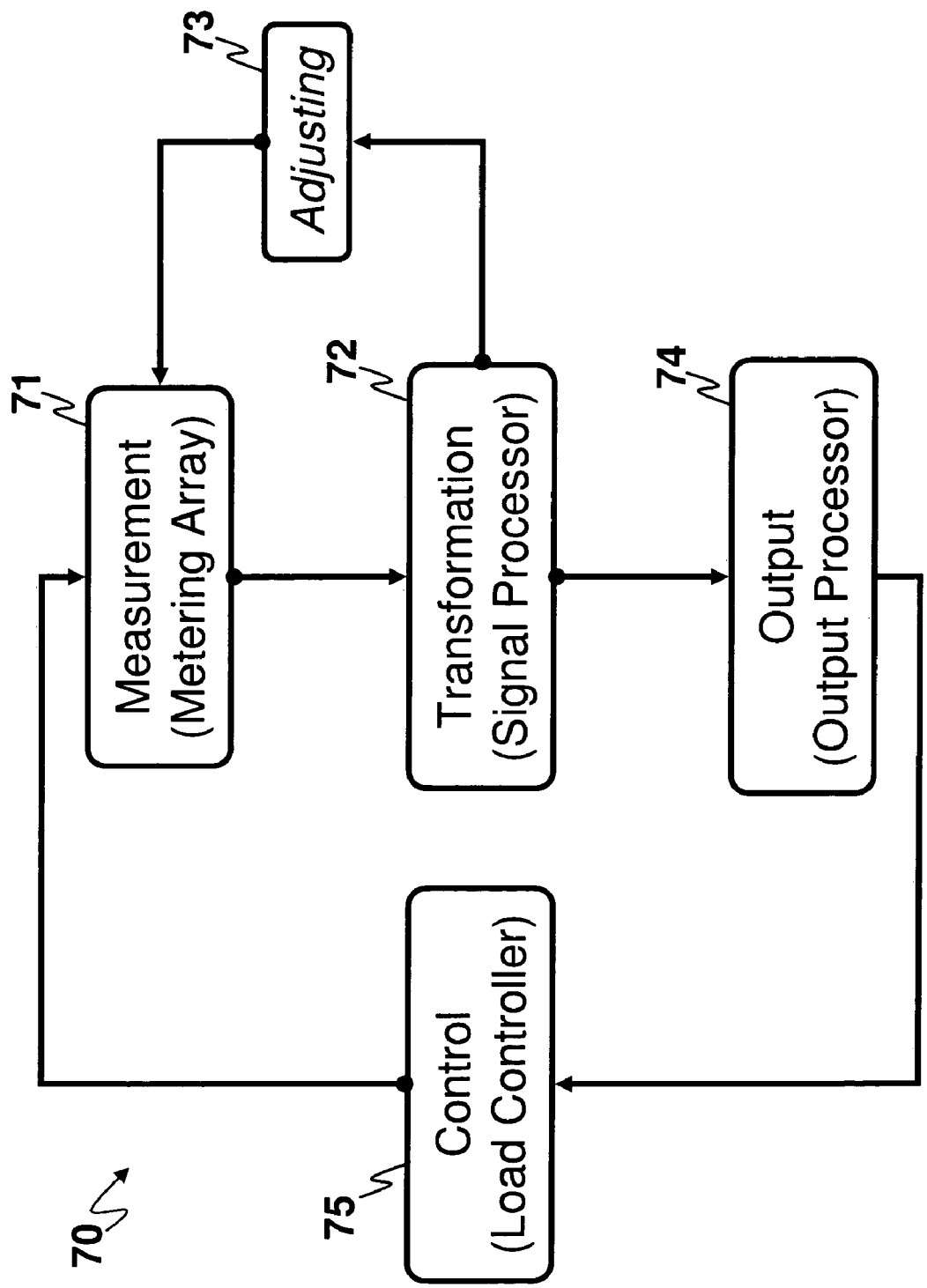
FIG. 7A is a flowchart showing a structural testing method according to this invention.
Figure 7B:
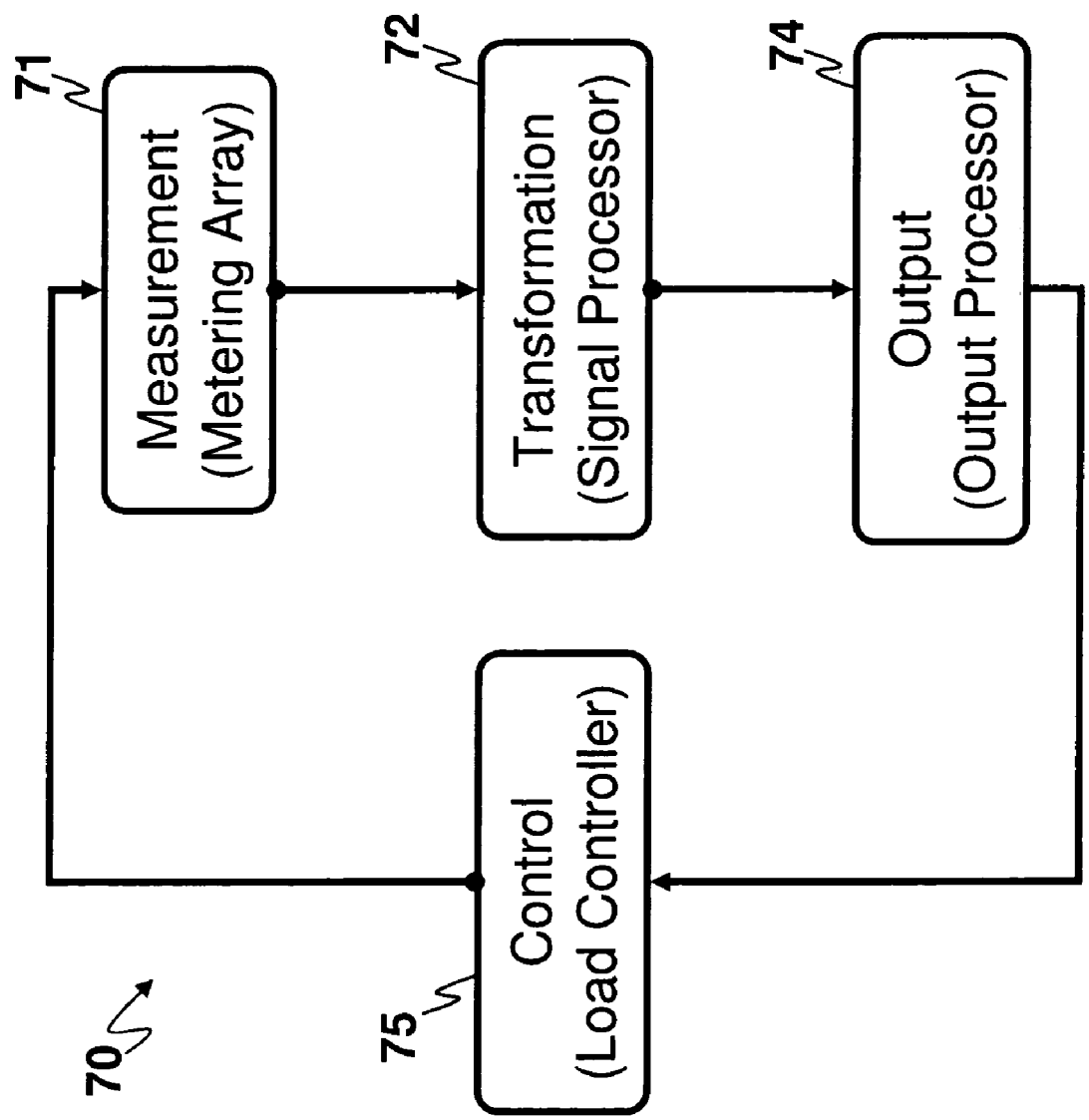
FIG. 7B is a flowchart showing a structural testing method according to this invention, where the method does not comprise adjusting.

FIG. 7A is a flowchart showing structural testing method 70, which may be non-destructive or destructive. Structural testing method 70 comprises measurement 71 of physical quantities associated with the structural element, transformation 72 of the measured physical quantities into sample mode spectra, adjusting 73 a set of sampling characteristics, output 74 and load control 75. In an alternate embodiment shown in FIG. 7B, method 70 does not comprise adjusting 73.

Measurement 71 comprises measurement of position, velocity, acceleration, angle, stress, strain, tension, torsion, vibrational frequency, temperature, pressure, or other physical quantity associated with the structural element. Transformation 72 comprises a signal transform of some measurements into a series of sample mode spectra and an averaging transform of other measurements into physical parameters. Transformation 72 optionally transforms some measurements into a series of baseline spectra, and some measurements into a series of sample mode spectra.

In one embodiment, transformation 72 comprises a signal transform that is a fast Fourier transform of accelerometer measurements relevant to a low-frequency structural oscillation. In this embodiment method 70 may employ a set of sampling characteristics including a sampling period of less than one second, preferentially on the order of hundredths of seconds, a scale sensitivity dependent upon the amplitude of oscillation, and a transformation window spanning at least one oscillation cycle, preferentially a number of cycles. In a preferred embodiment that comprises adjusting 73, a series of baseline spectra are acquired and the set of sampling characteristics are adjusted according to the baseline spectra. This provides method 70 with increased sensitivity to the onset of failure in a particular structural element.

Output 74 comprises generation of output based on a function of the sample mode spectra. The output characterizes an oscillation mode or oscillation modes with respect to relevant physical parameters such as load, cantilever length, temperature, or time. Optionally, output 74 comprises an alarm based on an alarm-generating function of the series of sample mode spectra as described above.

Load control 75 imposes mechanical load conditions under which the onset of structural failure may be detected by structural testing method 70. Load control 75 may comprise control of a compressive load or a more general stress, strain, tension, torsion, pressure, or other mechanical load, or a combination of loads. Load control 75 may further comprise control of physical quantities that directly or indirectly relate to the structural element's capability to sustain a load, such a temperature or cantilever length.

Structural testing method 70 has important advantages. In non-destructive testing, method 70 can detect the onset of structural failure before it occurs, even where actual failure points are unknown. In this embodiment output 74 includes an alarm that comprises an electronic signal to limit load control, allowing method 70 to prevent unanticipated and expensive or potentially hazardous failure in a test structure.

In destructive testing method 70 does not prevent structural failure, but rather generates sample mode spectra that characterize the onset and progress of structural failure. These sample mode spectra may be utilized for design improvements, to facilitate future non-destructive testing, or in a calibration for a method of structural health monitoring.

Structural testing method 70 may further comprise a part of a periodic maintenance program. The periodic maintenance program may be directed toward a structural element of a vehicle such as an aircraft. In this embodiment adjusting 73 may be performed at an initial application of method 70. In this initial application a series of baseline spectra are obtained and the set of sampling characteristics are adjusted according to the baseline spectra.

Figure 8A:
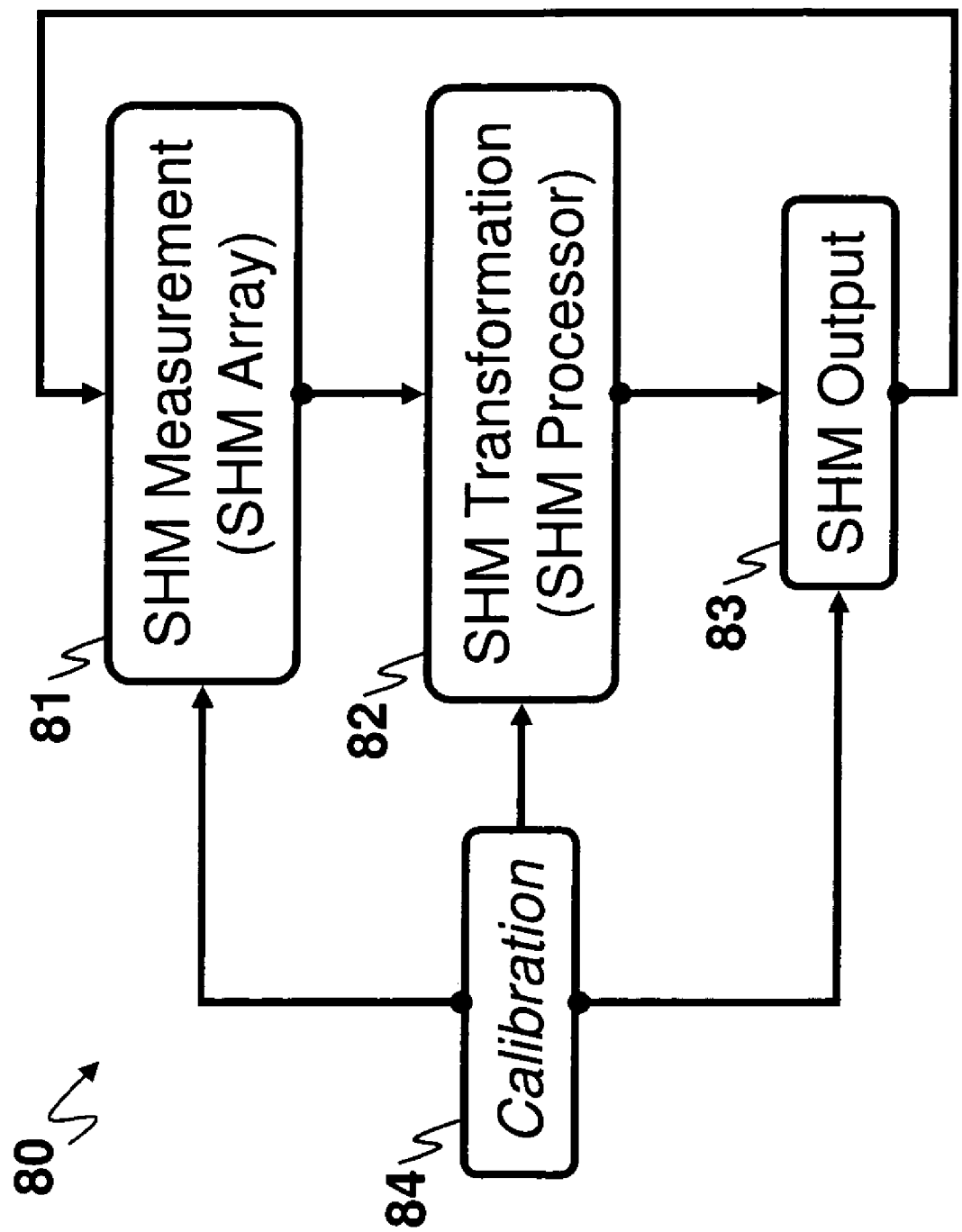
FIG. 8A is a flowchart showing a structural health monitoring method according to this invention.
Figure 8B:
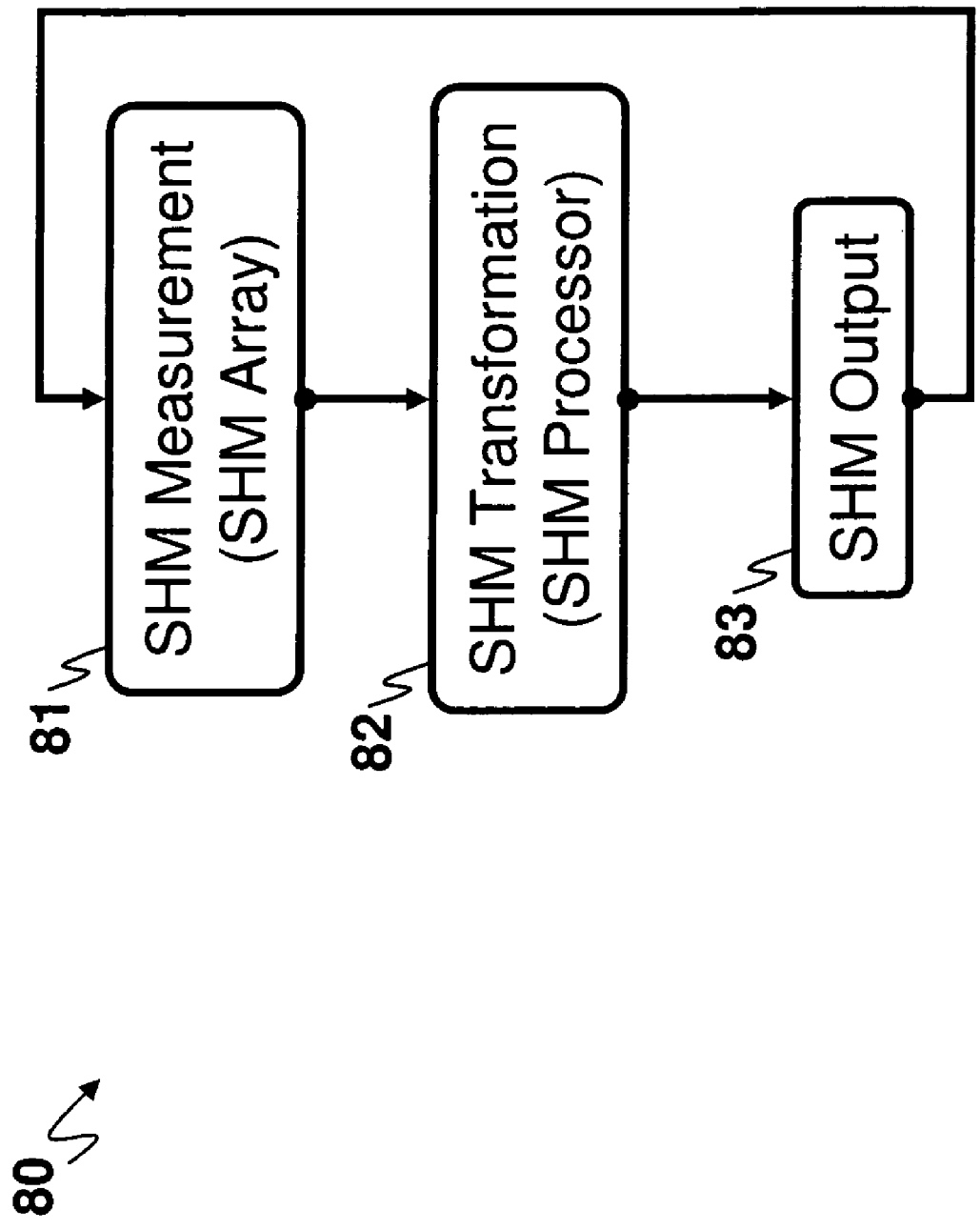
FIG. 8B is a flowchart showing a structural health monitoring method according to this invention, where the method does not comprise calibration.

FIG. 8A is a flowchart showing structural health monitor (SHM) method 80, which comprises measurement 81, transformation 82, output 83, and calibration 84. SHM method 80 detects the onset of structural failure in a composite structure, which may be composed of various structural elements and may be a prototype, a lifting apparatus, a building or portion thereof, a vehicle or portion thereof, or other composite structure. In an alternate embodiment shown in FIG. 8B, method 80 does not comprise calibration 84.

SHM measurement 81 is accomplished by an SHM array, which is a form of metering array. The SHM array will in general comprise a number of different sensor elements, positioned to measure a number of different physical quantities associated with the various structural elements comprising the composite structure.

SHM transformation 82 is accomplished by an SHM signal processor, which is a form of signal processor. SHM transformation 82 comprises a number of different signal transforms, as appropriate to the various SHM measurements characterizing oscillation modes. SHM transformation 82 further comprises a number of averaging transforms, as appropriate to the various SHM measurements characterizing physical parameters upon which the oscillation modes may depend. SHM transformation 82 optionally transforms some SHM measurements into a series of baseline spectra, and other SHM measurements into a series of sample mode spectra.

SHM output 83 comprises generation of output as a function of the sample mode spectra. SHM output 83 characterizes oscillation modes exhibited by the composite structure in terms of relevant physical parameters, and includes an alarm based upon a composite alarm-generating function, as appropriate to the various oscillation modes exhibited by the composite structure.

In a preferred embodiment, the SHM method comprises calibration 84 by structural testing method 70, which method may be either non-destructive or destructive. In this preferred embodiment, the output of structural testing method 70 is a set of calibration data, which characterizes the onset of structural failure in particular structural elements. In this preferred embodiment the set of calibration data may further be used to adjust a set of sampling characteristics relevant to SHM measurement 81 and SHM transformation 82, and in SHM output 83 as a basis for the composite alarm-generating function.

SHM method 80 illustrates additional advantages with respect to prior art SHM systems. Prior art SHM systems can detect local structural failures such as delamination and cracking, but only after they occur. SHM method 80 can detect the onset of such structural failures before they occur, even on a local scale, providing protection not only of the composite structure but also its individual elements.

Moreover, prior art SHM methods rely on monitoring techniques such as active Lamb wave interrogation that are physically and operationally distinct from those employed during structural testing. In contrast, in an embodiment that comprises calibration 84, calibration 84 employs the same techniques as SHM method 80, and can characterize the response of relevant structural elements not only to design stresses, but also to the onset of structural failure, and, in an embodiment where calibration 84 comprises destructive testing, to actual structural failure. This allows a preferred embodiment of SHM method 80 comprising calibration 84 to detect a range of unanticipated failure modes due to manufacturing defects, improper construction or maintenance, unanticipated load conditions, environmental extremes, or any other influence that may affect the characteristic oscillation modes of the composite structure.

The terminology used herein is for the purpose of description, not limitation. Specific structural and functional details disclosed herein are not to be interpreted as limiting, but merely as bases for teaching one skilled in the art to variously employ the present invention. Although the present invention has been described with reference to preferred embodiments, workers skilled in the art will recognize that changes may be made in form and detail without departing from the spirit and scope of the invention.

The invention claimed is:

1. A system for detecting onset of structural failure in a structural element subject to a mechanical load, the system comprising:
a metering away positioned for providing measurements of physical quantities associated with the structural element;
a signal processor for transforming the measurements into a series of sample mode spectra characterizing a natural oscillation frequency of the structural element; and
an output processor for generating an output indicating the onset of structural failure as a function of a shift in the natural oscillation frequency near a critical point of the structural element, wherein the shift in the natural oscillation frequency comprises a shift toward zero frequency near the critical point.

2. The system of claim 1, wherein the structural element comprises at least one of a beam, post, pipe, wall, pressure vessel, vane, blade, or housing, and the natural oscillation frequency is subsonic.

3. The system of claim 2, wherein the structural element is a composite structure, comprising a plurality of structural elements.

4. The system of claim 2, wherein the mechanical load comprises at least one of a compressive, stress, strain, tension, torsion or pressure load, and wherein the shift in the natural oscillation frequency near the critical point depends upon the mechanical load.

5. The system of claim 1, wherein the metering away includes at least one of a position sensor, velocity sensor, accelerometer, angular sensor, stress gauge, strain gauge, subsonic sensor, audio sensor, ultrasonic sensor, laser vibrometer, optical sensor, temperature sensor, or pressure sensor.

6. The system of claim 1, wherein the natural oscillation frequency is a lowest natural frequency of oscillation for the structural element.

7. The system of claim 1, wherein the signal processor transforms the measurements into the series of sample mode spectra via a fast Fourier transform.

8. The system of claim 1, wherein the shift in the natural oscillation frequency comprises a divergence from a loaded frequency curve near the critical point.

9. The system of claim 8, wherein the divergence is with respect to an analytical model of the loaded frequency curve.

10. The system of claim 1, wherein the output characterizes the natural oscillation frequency with respect to time and the output comprises a derivative of the series of sample mode spectra.

11. The system of claim 1, additionally comprising a driving force element mechanically coupled to the structural element.

12. The system of claim 1, additionally comprising a load controller coupled to the mechanical load.

13. The system of claim 12, wherein the system comprises a portion of a structural testing apparatus.

14. The system of claim 1, wherein the system comprises a portion of a structural health monitor.

15. A method for detecting onset of structural failure in a structural element subject to a mechanical load, the method comprising:
measuring physical quantities associated with the structural element;
transforming the measured physical quantities into a series of sample mode spectra characterizing a subsonic natural frequency of oscillation of the structural element; and
generating an alarm as a function of a variation in the series of sample mode spectra near a critical point of the structural element, wherein the variation in the series of sample mode spectra comprises a shift in the subsonic natural frequency of oscillation toward zero frequency near the critical point.

16. The method of claim 15, wherein the measured physical quantities are representative of at least one of position, velocity, acceleration, angle, stress, strain, tension, torsion, vibrational frequency, temperature or pressure.

17. The method of claim 15, wherein the measured physical quantities are transformed via one of a fast Fourier transform or a wavelet transform.

18. The method of claim 15, wherein the series of sample mode spectra characterize a fundamental mode of oscillation of the structural element and a higher-order mode of oscillation of the structural element.

19. The method of claim 15, wherein the variation in the series of sample mode spectra comprises an approach to an unbounded period of oscillation near the critical point.

20. The method of claim 19, wherein the variation in the series of sample mode spectra comprises an approach to an unbounded slope in frequency near the critical point.

21. The method of claim 19, wherein the variation in the series of sample mode spectra comprises a variation with respect to a series of baseline spectra.

22. The method of claim 19, wherein the variation in the series of sample mode spectra comprises a derivative of the series of sample mode spectra.

23. A method for structural testing of a structural element subject to a mechanical load, the method comprising:
measuring physical quantities associated with the structural element;
transforming some of the measured physical quantities into a series of sample mode spectra characterizing a natural frequency of a fundamental mode of oscillation of the structural element;
generating an output as a function of a variation in the series of sample mode spectra near a critical point of the structural element, wherein the shift in the series of sample mode spectra comprises a shift in the natural frequency of the fundamental mode of oscillation toward zero frequency near the critical point; and
controlling the mechanical load to detect onset of structural failure in the structural element, as a function of the output.

24. The method of claim 23, wherein the mechanical load comprises at least one of a compressive, stress, strain, tension, torsion, or pressure load, and wherein the shift in the natural oscillation frequency near the critical point depends upon the mechanical load.

25. The method of claim 23, wherein transforming some of the measured physical quantities additionally comprises transforming some of the measured physical quantities into a series of baseline spectra characterizing the fundamental mode of oscillation.

26. The method of claim 25, additionally comprising: adjusting a set of sampling characteristics according to the baseline spectra, in order to provide increased sensitivity to the onset of structural failure in the structural element.

27. The method of claim 26, wherein the set of sampling characteristics comprises at least one of scale sensitivity, sampling period, integration time, or transformation window.

28. The method of claim 23, wherein the method is performed as part of a non-destructive testing process in which controlling the mechanical load is limited as a function of the output, in order to prevent structural failure of the structural element.

29. The method of claim 23, wherein the method is performed as part of a destructive testing process in which the output characterizes the onset and progress of structural failure in the structural element.

30. The method of claim 23, wherein the method is performed as part of a periodic inspection program.

31. The method of claim 30, wherein the structural element is a structural element of an aircraft.

32. The method of claim 23, wherein the output comprises an alarm based on the variation in the series of sample mode spectra.

33. The method of claim 32, wherein the alarm comprises at least one of an audible, visual, or electronic alarm.

34. The method of claim 32, wherein the alarm comprises an electronic signal to limit controlling the mechanical load.

35. A method for structural health monitoring, the method comprising:
measuring physical quantities associated with a composite structural element;
transforming the measured physical quantities into a series of sample mode spectra characterizing a natural frequency of oscillation of the composite structural element; and
generating an output as a function of the series of sample mode spectra, wherein the output comprises an alarm based upon an alarm-generating function of the sample mode spectra near a critical point of the composite structural element, and wherein the alarm-generating function comprises a shift in the natural frequency of oscillation toward zero frequency near the critical point.

36. The method of claim 35, wherein the alarm-generating function comprises a derivative of the natural frequency of oscillation near the critical point.

37. The method of claim 35, additionally comprising: calibrating the structural health monitoring method by adjusting a sampling characteristic using calibration data, in order to provide increased sensitivity to onset of structural failure in the composite structural element.

38. The method of claim 35, wherein the alarm-generating function comprises a divergence of the natural frequency of oscillation from a loaded frequency curve near the critical point.

* * * * *